US008518424B2

United States Patent
Sasaki et al.

(10) Patent No.: US 8,518,424 B2
(45) Date of Patent: *Aug. 27, 2013

(54) RESIN POWDER FOR DERMATOLOGIC COMPOSITION, SKIN CLEANSING AGENT AND COSMETIC COMPOSITION USING THE POWDER, AND PREPARATION PROCESSES OF THE POWDER

(75) Inventors: Yuki Sasaki, Minamiashigara (JP); Yasuo Matsumura, Minamiashigara (JP); Takayoshi Aoki, Minamiashigara (JP); Etsuo Tominaga, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 754 days.

This patent is subject to a terminal disclaimer.

(21) Appl. No.: 11/850,034

(22) Filed: Sep. 5, 2007

(65) Prior Publication Data

US 2007/0298062 A1    Dec. 27, 2007

Related U.S. Application Data

(62) Division of application No. 10/015,611, filed on Dec. 17, 2001, now abandoned.

(30) Foreign Application Priority Data

Aug. 17, 2001 (JP) ................. 2001-248322

(51) Int. Cl.
*A61K 8/02* (2006.01)
*A61K 9/14* (2006.01)
*A61K 8/72* (2006.01)
*A61K 31/74* (2006.01)

(52) U.S. Cl.
USPC ..... 424/401; 424/489; 424/70.11; 424/78.02; 424/78.03

(58) Field of Classification Search
None
See application file for complete search history.

(56) References Cited

U.S. PATENT DOCUMENTS

| 5,827,590 A | * | 10/1998 | Morita et al. ............. 428/40.1 |
| 5,849,456 A | | 12/1998 | Matsumura et al. |
| 5,859,069 A | | 1/1999 | Yanagida |
| 5,976,750 A | | 11/1999 | Hagi et al. |
| 6,017,552 A | * | 1/2000 | Mori ........................... 424/401 |
| 6,080,519 A | | 6/2000 | Ishiyama et al. |
| 6,153,346 A | | 11/2000 | Maehata et al. |
| 6,329,114 B1 | | 12/2001 | Watanabe et al. |
| 6,503,983 B1 | | 1/2003 | Morrison et al. |
| 6,576,623 B1 | | 6/2003 | Nakanishi et al. |
| 6,686,112 B2 | | 2/2004 | Teshima et al. |
| 6,893,649 B2 | * | 5/2005 | Sasaki et al. .............. 424/401 |
| 2001/0053492 A1 | | 12/2001 | Suwabe et al. |
| 2003/0073021 A1 | | 4/2003 | Sasaki et al. |

FOREIGN PATENT DOCUMENTS

| DE | 197 35 225 A1 | 2/1999 |
| EP | 0 834 305 B1 | 4/1998 |
| EP | 1 072 627 B1 | 1/2001 |
| JP | 05-310530 A | 11/1993 |
| JP | 08-225316 A | 9/1996 |
| JP | 10-338616 | 12/1998 |
| JP | 11-130617 A | 5/1999 |
| JP | 2000-242032 A | 9/2000 |
| JP | 2000-267334 A | 9/2000 |
| JP | 2001-117263 A | 4/2001 |
| JP | 2001-151640 A | 6/2001 |
| JP | A 2001-151639 | 6/2001 |
| JP | 2001-213727 A | 8/2001 |
| JP | 2001-213753 A | 8/2001 |

OTHER PUBLICATIONS

Derwent Abstract of JP 06-070702 (Mar. 15, 1994).
Machine Translation of JP 2001-151639 (Jun. 5, 2001).
English Translation of German Office Action.
Material Safety Data Sheet for White Petrolatum.
Material Safety Data Sheet for Petroleum Jelly.

* cited by examiner

Primary Examiner — Sreeni Padmanabhan
Assistant Examiner — Jody Karol
(74) Attorney, Agent, or Firm — Oliff & Berridge, PLC

(57) ABSTRACT

Provided is a resin powder for a dermatologic composition composed of resin particles having an average volume particle size of 2.0 to 20.0 µm, a shape factor SF1 of 110 to 140 and an average volume particle size distribution GSDv of 1.3 or less. Also disclosed are a skin cleansing composition and a cosmetic composition containing the resin powder, and a preparation process of the resin powder.

22 Claims, 1 Drawing Sheet

RESIN POWDER FOR DERMATOLOGIC COMPOSITION, SKIN CLEANSING AGENT AND COSMETIC COMPOSITION USING THE POWDER, AND PREPARATION PROCESSES OF THE POWDER

This application is a divisional of application Ser. No. 10/015,611, filed Dec. 17, 2001, which is incorporated herein by reference in its entirety.

FIELD OF THE INVENTION

The present invention relates to a resin powder for a dermatologic skin composition. The invention also relates to a skin cleansing agent and cosmetic composition containing the resin powder and a preparation process of the resin powder.

BACKGROUND OF THE INVENTION

With regard to powder-containing cosmetic compositions such as foundation, eye shadow, baby powder, emulsion, antiperspirant powder and body shampoo, addition of a spherical resin powder and moreover an improvement in a resin to be added have conventionally been conducted in order to improve its smoothness and spreadability upon application, affinity to the skin and refreshing coolness after use.

For example, JP-A-2001-151639 discloses a cosmetic composition comprising spherical fine particles made of polystyrene, etc.

The above-described composition is however accompanied with the following problems.

Specifically, the above-described spherical fine particles have a particle size distribution (CV) of 15% or less, meaning that the particles are almost truly spherical. So the cosmetic composition has good spreadability upon application, but skin adhesion or affinity to the skin necessary upon its application becomes insufficient, tending to cause makeup to comes off.

Such spherical resin powder particles are usually prepared by emulsion polymerization or suspension polymerization, which method however markedly widens the particle size distribution of the resin powder and permits preparation of only truly spherical particles.

SUMMARY OF THE INVENTION

The present invention has been made in view of the foregoing problems.

Accordingly, an object of the invention is to provide a resin powder for dermatologic composition capable of attaining sufficient spreadability and skin adhesion upon application of a cosmetic composition, a skin cleansing composition or the like to the skin.

Another object of the invention is to provide a skin cleansing composition containing the resin powder.

A still other object of the invention is to provide a cosmetic composition containing the resin powder.

A still other object of the invention is to provide a process for preparing the resin powder.

Other objects and effects of the present invention will become apparent from the following description.

The present inventors have carried out an extensive investigation to attain the above-described objects. As a result, it has been found that the above-described objects can be achieved by setting each of the shape factor SF1, average volume particle size, and average volume particle size distribution GSDv of resin particles to a specific range, leading to the completion of the invention.

Specifically, the present invention relates to a resin powder for a dermatologic composition, which comprises resin particles having an average volume particle size of 2.0 to 20.0 µm, a shape factor SF1 of 110 to 140 and an average volume particle size distribution GSDv of 1.3 or less.

The represent invention also relates to a cosmetic composition comprising the above-described resin powder for a dermatologic composition.

The present invention also relates to a skin cleansing composition comprising the above-described resin powder for a dermatologic composition.

The present invention further relates to a process for preparing the above-described resin powder for a dermatologic composition, which comprises preparing a dispersion of resin particles by emulsion polymerization and allowing the resin particles to undergo agglomeration.

DETAILED DESCRIPTION OF THE INVENTION

Embodiments of the present invention are described in detail below.

In the resin powder for a dermatologic composition according to the invention, resin particles have an average volume particle size of 2.0 to 20.0 µm, preferably 2.0 to 15.0 µm. A cosmetic composition or skin cleansing composition containing resin particles having a particle size outside the above-described range is deteriorated in usability such as spreadability. Particularly when the particle size exceeds 20 µm, foreign body sensation appears upon use and, moreover, coming off of makeup may be brought about. When resin particles having a particle size less than 2.0 µm are added to a cleansing agent, on the other hand, they do not remain on the skin effectively and particularly in the case of the resin particles having fine particles adhered to the surface thereof, lower the adhesion strength of the fine particles to the resin particles and decrease the adhesion amount, thereby inhibiting exhibition of the function of the fine particles.

Figure 1:
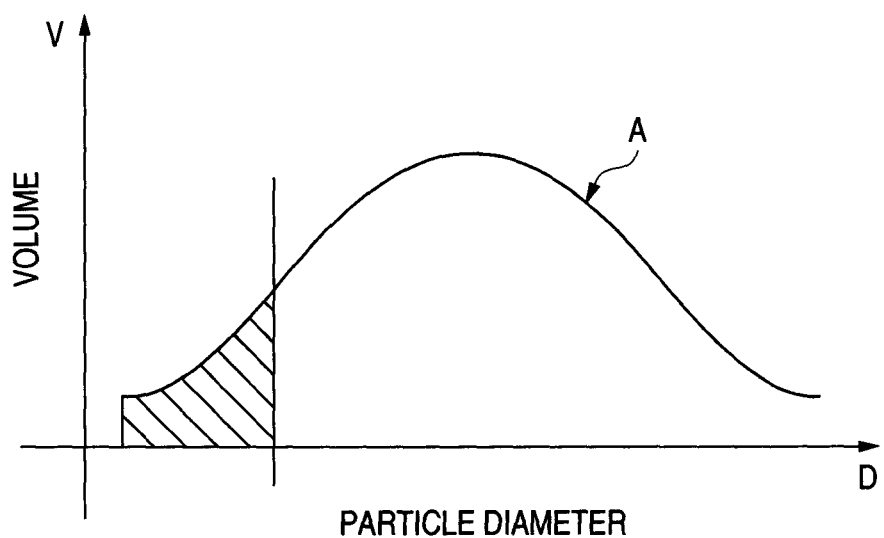
FIG. 1 is a graph illustrating a relation between particle size and volume of resin particles.

The average volume particle size distribution GSDv of the resin powder for dermatologic composition according to the invention is 1.3 or less. The "average volume particle size distribution GSDv" as used herein is defined by the following formula using the cumulative distributions D16 and D84.

$$GSDv = (\text{volume } D84/\text{volume } D16)^{0.5}$$

wherein, in the case where, in the graph as shown in FIG. 1, the area between the curve A and the axis D is presumed as a whole powder volume and a straight line is drawn in parallel to the axis V so that the shaded area be X % of the whole volume, the volume DX means a value of D (particle size) where the straight line intersects the axis D.

If this GSDv exceeds 1.3, the particle size becomes irregular, by which effects such as spreadability upon application and refreshing coolness cannot be brought about.

The particles of the resin powder for dermatologic composition according to the invention have a shape factor SF1 of 110 to 140. The "shape factor SF1" of resin particles as used herein means a value as defined by the following formula:

$$SF1 = (\pi \times (ML/2)^2 / A) \times 100$$

wherein, ML means the maximum length (absolute maximum length) of resin particles and A means a projected area of resin particles. The term "projected area of resin particles" means an area of resin particles projected onto a circle having the maximum length of resin particles as a diameter. As the shape factor SF1 approaches 100, the resin particles are of a truer sphere. The greater it becomes, on the other hand, the more unevenness appears on the surface and the shape of the resin particles is farther from a true sphere.

At a shape factor SF1 less than 110, the resin particles have an almost truly spherical form and spreadability upon application is improved, but skin adhesion or affinity required upon application of a cosmetic composition becomes insufficient. Thus, spreadability and skin adhesion upon application cannot be attained simultaneously at such an excessively small shape factor.

When the shape factor SF1 exceeds 140, unevenness appears on the surface of the resin particles, which improves skin adhesion. Spreadability upon application on the other hand becomes insufficient.

The upper limit of the shape factor SF1 is preferably 130, more preferably 120. When the shape factor SF1 is 130 or less, the resin particles approach a true sphere, making it possible to improve their fluidity on the skin surface and smoothness upon application of, for example, a makeup cosmetic composition containing them, and permitting uniform application onto the skin.

The shape factor SF1 is calculated by analyzing a microscopic image or scanning electron microscopic image by an image analyzer ("LUZEX III", manufactured by Nireco Corporation), measuring the maximum length ML and projected area A of resin particles and substituting them in the above-described formula.

In the resin powder for dermatologic composition according to the invention, a surfaceness index of the resin particles is preferably 2.0 or less. The term "surfaceness index" of the resin particles as used herein is defined by the following formula:

(Surfaceness index)=(specific surface area measured)/
(specific surface area calculated)

(Specific surface area calculated)=$6\Sigma(n \times R^2)/\{\rho \times \Sigma(n \times R^3)\}$ wherein, n means the number of particles in the channel of a Coulter counter, R is the diameter (μm) of the channel of the Coulter counter and ρ is a density of resin particles (g/cm$^3$).

The term "Coulter counter" as used herein means "TA-II" manufactured by Nikkaki Co. The specific surface area measured is a BET specific surface area measured using "Flow Sorb 2300" manufactured by SHIMADZU CORP. As the surfaceness index is closer to 1.0, the surface of the resin particles approaches complete smoothness. At a surfaceness index exceeding 2.0, the surface of the resin particles becomes too rough, tending to lower the usability (spreadability) when they are incorporated in a cosmetic composition.

In the resin powder for dermatologic composition according to the invention, the average number particle size distribution GSDp of the resin particles is preferably 1.5 or less. The term "average number particle size distribution GSDp" as used herein is defined by the following formula using cumulative distributions D16 and D84.

Figure 2:
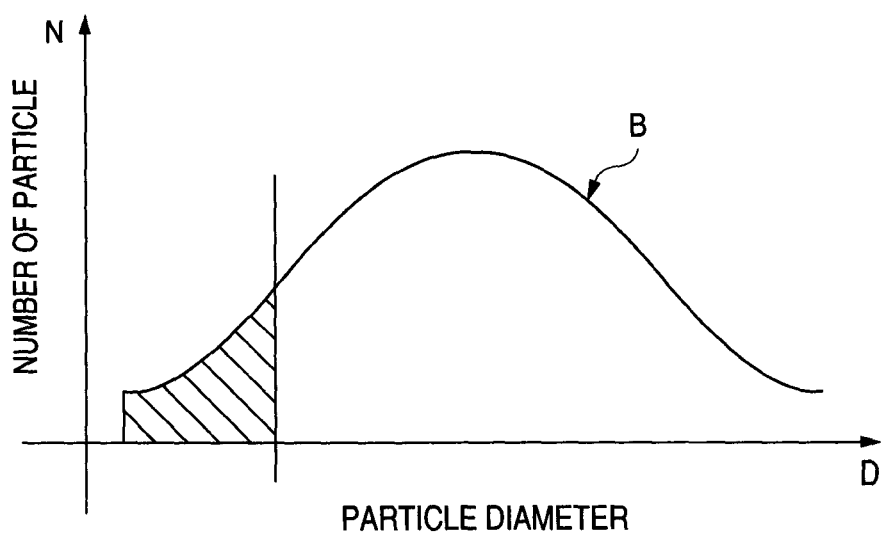
FIG. 2 is a graph illustrating a relation between particle size and the number of resin particles.

$GSDp=(\text{number } D84/\text{number } D16)^{0.5}$ wherein, in the case where, in the graph as shown in FIG. 2, the area between the curve of B and the axis D is presumed as a whole particle number and a straight line is drawn in parallel to the axis N so that the area of the shaded portion be X % of the whole particle number, the number DX means a value of D (particle size) where the straight line crosses with the axis D.

If this GSDp exceeds 1.5, the particle size becomes uneven, by which effects such as spreadability upon using and refreshing coolness cannot be brought about.

In the resin powder according to the invention, a ratio (volumetric ratio) of particles having a volume particle size of 20 μm or greater is preferably 3% or less. When a ratio of particles having a volume particle size of 20 μm or greater is 3% or greater, the resulting composition does not smoothly spread on the skin and uniformity upon application tends to be lost. This tendency becomes eminent when the average volume particle size of the resin particles becomes smaller and the surfaceness index approaches 1.0.

The resin constituting the resin particles used in the invention preferably has a number-average molecular weight of 3000 to 20000. The term "number-average molecular weight" as used herein means a molecular weight as measured using a molecular weight analyzer ("HLC-8120" manufactured by TOSOH CORP). Number-average molecular weights less than 3000 tend to cause agglomeration of resin particles and soften the resin, thereby interfering with usability and storage stability. Number-average molecular weights exceeding 20000, on the other hand, tend to make the resin particles too hard, thereby interfering with usability and storage stability (described specifically, when these resin particles are incorporated in a cosmetic composition, the resulting composition is reduced in the affinity to the skin and imparts the skin with tautness).

The resin constituting the resin particles preferably has a weight-average molecular weight of 6000 to 100000. The term "weight-average molecular weight" as used herein means a molecular weight as measured using a molecular weight analyzer ("HLC-8120", trade name; manufactured by TOSOH CORP) with THF as a solvent. Weight-average molecular weights less than 6000 tend to cause agglomeration of resin particles and soften the resin, thereby interfering with usability and storage stability. Number-average molecular weights exceeding 100000, on the other hand, tend to make the resin particles too hard, thereby interfering with usability and storage stability (described specifically, when these resin particles are incorporated in a cosmetic composition, the resulting composition is reduced in affinity to the skin and imparts the skin with tautness).

The resin constituting the resin particles preferably has a glass transition temperature of 40 to 100° C. The term "glass transition temperature" as used herein means a temperature as measured using a differential scanning calorimeter ("DSC-50", trade name; product of SHIMADZU CORP) at a heating rate of 10° C./min. At a glass transition temperature less than 40° C., the resin softens excessively and tends to interfere with usability and storage stability. Glass transition temperatures exceeding 100° C., on the other hand, tend to make the resin particles too hard, thereby interfering with usability and storage stability (described specifically, when these resin particles are incorporated in a cosmetic composition, the resulting composition has reduced skin affinity and imparts the skin with tautness).

The resin powder according to the invention preferably has a compaction ratio of 0.6 or less. The term "compaction ratio" as used herein means a value calculated by substituting loosely-packed apparent specific gravity X and tightly-packed apparent specific gravity Y, as measured by a powder tester manufactured by Hosokawa Micron Ltd, in the following formula:

Compaction ratio=(tightly packed apparent specific gravity Y–loosely packed apparent specific gravity X)/(tightly packed apparent specific gravity Y).

The compaction ratio is a parameter indicating the degree of fluidity of resin particles. The lower the compaction ratio, the higher the fluidity of the resin particles and vice versa. Resin particles having a compaction ratio exceeding 0.6 lose fluidity, tending to disturb smooth application of the resulting composition to the skin.

The resin powder according to the invention preferably has a water content of 3 wt. % or less. The water content is also an important factor influencing on the fluidity of the resin particles. Water contents of the resin powder exceeding 3 wt. % decrease dry touch feeling and tends to deteriorate spreadability upon application. Incorporation of a resin powder having a water content of 3 wt. % or less improves fluidity of a dermatologic composition containing it. The water content can be measured in a known manner.

When a resin powder to be added to a cosmetic composition happens to contain impurities such as those derived from raw materials or residual monomers, not only usability of the resin powder lowers, but also quality or safety is adversely affected. It is therefore necessary to reduce the impurity content to the lowest level. Particularly, volatile components have an influence on another component upon preparation or use of the cosmetic composition and moreover, their offensive odor sometimes causes discomfort upon use. The volatile content in the resin powder is preferably suppressed to 100 ppm or less. The volatile content not exceeding 100 ppm usually causes neither an offensive odor nor a bad influence. Although there is no particular limitation imposed on the measuring method of the volatile content insofar as it is a conventional manner, measurement by chromatography is preferred.

An acid value has an influence on the anti-greasiness of a resin and at the same time, on adhesion and agglomeration between resin particles and another substance. In the resin powder for dermatologic composition according to the invention, the resin constituting the resin particles preferably has an acid value falling within a range of from 1.0 to 20 mg/KOH/g. A cosmetic composition containing resin particles constituted by such a resin can be washed way by an ordinarily employed soap or face wash. At an acid value falling within the above-described range, when fine particles are adhered to the surface of resin particles, a cosmetic composition or cleansing composition containing them has appropriate adhesion strength and the resin particles do not agglomerate each other.

In the resin powder for dermatologic composition according to the invention, surface tension of a solution, which is available by dissolving 1 g of the resin powder in 3 g of acetone, adding 25 g of deionized water to the resulting solution, and filtering off the precipitate thus formed, is preferably 20 mN or greater. When the surface tension is less than 20 mN, the amount of impurities increases, which tends to cause problems such as deterioration in storage stability, for example, generation of agglomerates upon storage, and emission of an offensive odor. The upper limit of the surface tension of the solution is 70 mN, because surface tension of the solution never exceeds 70 mN.

In the resin powder according to the invention, the conductivity of the above-described solution is preferably 100 µS or less. When the conductivity exceeds 100 µS, the amount of impurities increases, which tends to cause problems such as deterioration in storage stability, for example, generation of agglomerates upon storage, and emission of an offensive odor.

In the resin powder according to the invention, the above-described solution preferably has a surface tension of 20 mN or greater and conductivity of 100 µS or less. If so, problems such as deterioration in storage stability, for example, generation of agglomerates upon storage, and emission of an offensive odor do not occur. Accordingly such resin powder is suited as a component of a dermatologic composition.

No particular limitation is imposed on a resin to be used for resin particles of the invention. Specific examples include homopolymers of a monomer, for example, a styrene monomer such as styrene, p-chlorostyrene or α-methylstyrene, an acrylic monomer such as methyl acrylate, ethyl acrylate, n-propyl acrylate, lauryl acrylate or 2-ethylhexyl acrylate, a methacrylic monomer such as methyl methacrylate, ethyl methacrylate, n-propyl methacrylate, lauryl methacrylate or 2-ethylhexyl methacrylate, an ethylenically unsaturated acid monomer such as acrylic acid, methacrylic acid or sodium styrenesulfonate, a vinylnitrile such as acrylonitrile or methacrylonitrile, a vinyl ether such as vinyl methyl ether or vinyl isobutyl ether, a vinyl ketone such as vinyl methyl ketone, vinyl ethyl ketone or vinyl isopropenyl ketone or an olefin such as ethylene, propylene or butadiene; copolymers obtained from a combination of at least two of the above-exemplified monomers; a mixture of them; a non-vinyl-condensation type resin such as epoxy resin, polyester resin, polyurethane resin, polyamide resin, cellulose resin or polyether resin; a mixture thereof with the above-exemplified vinyl resin; and graft polymers available by polymerization of a vinyl monomer in the presence of them. Among them, as a resin to be incorporated in the dermatologic composition in order to impart the composition with its characteristics, styrene copolymers are preferred for high hardness, easy controllability of their molecular weight and glass transition temperature and low cost. As the styrene copolymer, a styrene-acrylate copolymer is particularly preferred, because it is excellent in its color, spreadability and smoothness and it can be produced stably at a low cost.

The resin powder of the invention has excellent spreadability and skin adhesion so that it is suitably added to various cosmetic compositions and skin cleansing compositions. No limitation is imposed on the cosmetic composition or skin cleansing composition insofar as it is an ordinarily employed powder-containing composition. Its formulation form is also not limited and examples include liquid, paste, O/W emulsion, W/O emulsion, gel, powder and solid.

Examples of the cosmetic composition include makeup cosmetic compositions such as foundation, lipstick, powder lip, lip gloss, cheek rouge, eye shadow, eye liner, mascara and dusting powder, baby powder, shaving lotion, shaving foam, calamine lotion, emulsion, cream, ointment, peel-off pack, antiperspirant, deodorant, hair treatment agent, permanent wave formulation, hair dye, hair setting lotion, hair tonic, hair growth tonic and baldness remedy. Examples of the cleansing composition include face wash cream, face wash powder, body shampoo, hair shampoo and hair rinse.

The resin powder for dermatologic composition according to the invention is preferably prepared by emulsion polymerization & agglomeration method.

In the emulsion polymerization and agglomeration method, a resin dispersion is prepared first by emulsion polymerization. Then, a coagulant is added to the resulting resin dispersion to agglomerate resin particles therein, whereby agglomerated particles having an intended particle size are formed. By heating them to the glass transition temperature of the resin or greater, the agglomerated particles are united by fusion. At this time, functional fine particles such as pigment, ultraviolet screening agent and infrared ray shielding agent can be added.

The resin powder is obtained by washing and drying the thus-obtained fused particles. Although there is no particular limitation imposed on the solid-liquid separation method after washing, suction filtration and pressure filtration are preferred for productivity. No particular limitation is imposed on the drying method, but vacuum lyophilization, jet flash drying, fluid drying and oscillation type fluid drying are preferred. By selecting the heating conditions upon preparation, the resin particles in the amorphous to spherical form are available.

The above-described process for uniting the agglomerated particles by fusion is usually conducted by mixing and agglomerating the resin dispersion and the like at one step. Since uniformly mixed agglomerated particles are united, the agglomerated particles usually have a uniform structure from their surface to their inside.

The resin powder of the invention may have another fine particles attached to the resin particles (resin particles having fine particles adhered to the surface thereof will hereinafter be called "fine-particle-adhered resin particles"). In this case, it is possible not only to prevent re-agglomeration of fine particles, but also to permit exhibition of a function derived from the fine particles while maintaining the usability derived from the resin particles. The size of the fine particles to be adhered to the resin particles depends on their amount to be adhered and the size of the resin particles. Particularly preferred is use, in combination, of resin particles and fine particles to satisfy the following formula: (particle size of resin particles)/(particle size of fine particles)$\geq$2. At this ratio less than 2, adhesion strength of fine particles to the resin particles tends to lower.

As the fine particles to be adhered to the resin particles, those ordinarily added to a cosmetic composition such as pigments, ultraviolet screening agents and infrared ray shielding agents are employed. Use of a pigment imparts the composition with uniform and durable coloring property, use of a ultraviolet screening agent imparts it with uniform and durable anti-sunburn effects due to its ultraviolet screening function and use of an infrared ray shielding agent imparts it with uniform and durable infrared-ray shielding effects. No limitation is imposed on the pigment insofar as it is ordinarily employed for cosmetic compositions or cleansing compositions. Examples include inorganic pigments such as iron oxide and aluminum silicate, organic pigments such as carbon black and extender pigments such as talc. Examples of the ultraviolet screening agent include inorganic compounds such as titanium oxide and cerium oxide and organic compounds such as benzophenone, benzotriazole and salicylic acid salts. Examples of the infrared ray shielding agent include titanium oxide, zirconium oxide and silicon carbide, and compounds thereof.

When metal compound fine particles are adhered to the surface of the resin particles, they exhibit excellent adhesion to the resin particles. Owing to exhibition of both a function brought by the resin as a lubricant and a function brought by the metal compound, the resulting dermatologic composition or cosmetic composition acquire synergistic effects. Described specifically, the composition can exhibit functions (fluidizing function, ultraviolet-ray absorbing function and storage-stability improving function) derived from the metal compound fine particles while maintaining smoothness, spreadability and skin affinity of the resin particles. As the metal compound, metal oxides ordinarily employed as a raw material for cosmetic compositions are usable and examples include, but not limited to, silicon dioxide, iron oxide (red oxide, black iron oxide), zirconium oxide and aluminum oxide.

A weak adhesive strength ratio of fine particles to the resin particles is preferably 90% or less. The term "weak adhesive strength ratio" as used herein means a ratio, to the amount of the metal compound in the whole resin powder, of the amount of the metal compound in a supernatant obtained by dispersing 2 g of a resin powder composed of fine-particle-adhered resin particles and a trace amount of a surfactant in 40 g of pure water, applying ultrasonic wave for 1 minute at 50 micron-ampere by an ultrasonic oscillator inserted in the dispersion and then centrifuging the dispersion. It expresses the adhesive strength of the fine particles to the resin particles. The greater the weak adhesive strength ratio, the weaker the adhesive force of the fine particles and vice versa. The amount of the metal compound in the supernatant and that in the whole resin powder composed of fine-particle-adhered resin particles can be determined by element analysis using fluorescent X-rays.

When a weak adhesive strength ratio as defined above exceeds 90%, usability of the dermatologic composition such as cosmetic composition or skin cleansing composition tends to lower because of weak adhesive force of the fine particles to the surface of the resin particles. In addition, there is a potential danger that the fine particles released from the resin particles may have an influence on another component. A weak adhesive strength ratio is preferably 50% or less.

A weight ratio of the fine particles to the resin particles usually falls within a range of 0.1 to 90 wt. %, preferably 0.1 to 60 wt. %. When the weight ratio is less than 0.1 wt. %, the fine particles do not tend to exhibit their functions fully because of their small content. Addition of them in an amount exceeding 90 wt. % does not increase the content of the fine particles relative to the resin particles because the fine particles flake off.

Although the amount of the resin powder to be incorporated in the cosmetic composition or skin cleansing composition differs with its using purpose, the amount usually ranges from 0.1 to 90 wt. %, preferably 0.5 to 60 wt. %. At an amount less than 0.1 wt. %, effects of the resin powder do not appear readily, while even at an amount exceeding 90 wt. %, effects of the resin powder given to the cosmetic composition or cleansing composition do not increase in proportion.

Upon incorporation of the resin powder and/or resin powder made of fine-particle-adhered resin particles in a cosmetic composition, the other components to be incorporated therein are selected according to the using purpose of the cosmetic composition and are not limited specifically. Examples include inorganic powders such as talc, kaolin, mica, sericite, magnesium carbonate, calcium carbonate, aluminum silicate, barium silicate, calcium silicate, magnesium silicate, magnesium, silica, zeolite, barium sulfate and calcium phosphate, organic powders such as silicone resin powders and cellulose powders, pearlescent pigments such as titanium dioxide, zinc oxide, iron oxide, iron titanate, yellow oxide, carbon black, titanium monoxide, bismuth oxychloride and fish scale guanine, metal powder pigments such as aluminum powder and copper powder, organic pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 405, Red No. 505, Orange No. 204, Orange No. 205, Yellow No. 4, Yellow No. 5, Yellow No. 202, Yellow No. 203, Yellow No. 205, Yellow No. 401 and Blue No. 404, and natural pigments such as chlorophyll and β-carotene.

The resin powder may be incorporated after treatment with silicone, metal soap, fatty acid, surfactant, acid, alkali or inorganic salt, or combination thereof.

Examples of a further component to be incorporated in a cosmetic composition or skin cleansing composition include hydrocarbons such as squalane, vaseline and liquid paraffin, oils such as higher fatty acids or oils and fats including camellia oil and olive oil, esters, and higher alcohols, surfactants, antiperspirants, bactericides, water, antiseptics and thickeners.

The cosmetic composition or skin cleansing composition of the invention can be prepared in a conventional manner.

The present invention will be illustrated in greater detail with reference to the following Examples and Comparative Examples, but the invention should not be construed as being limited thereto.

Preparation of Resin Dispersion 1

In a flask, a solution obtained by mixing styrene, n-butyl acrylate, acrylic acid and dodecanethiol (which will hereinafter be abbreviated as "DDT") in amounts as shown below in Table 1 was dispersed and emulsified in a solution obtained by dissolving 13 g of an anionic surfactant, "Neogen R" (sodium dodecylbenzene sulfonate; product of Daiichi Pharmaceutical Co., Ltd.) in 555 g of deionized water. While gradually stirring the mixture for 10 minutes, 42.8 g of deionized water having 9 g of ammonium persulfate dissolved therein was charged in the flask for purging with nitrogen. Over an oil bath, the reaction mixture in the flask was then heated until it became 70° C. while stirring. Emulsion polymerization was continued as was for 6 hours, whereby Resin Dispersion 1 was obtained.

TABLE 1

| Amount (g) | Resin dispersion 1 | Resin Dispersion 2 | Resin Dispersion 3 |
| --- | --- | --- | --- |
| Styrene | 540 | 400 | 480 |
| n-Butyl acrylate | 60 | 200 | 120 |
| Acrylic acid | 12 | 18 | 36 |
| DDT | 12 | 24 | 3 |

Preparation of Resin Dispersion 2

In a similar manner to that employed for Resin Dispersion 1 except that the amounts of styrene, n-butyl acrylate, acrylic acid and DDT were changed as described above in Table 1, Resin Dispersion 2 was obtained.

Preparation of Resin Dispersion 3

In a similar manner to that employed for Resin Dispersion 1 except that the amounts of styrene, n-butyl acrylate, acrylic acid and DDT were changed as described above in Table 1, Resin Dispersion 3 was obtained.

EXAMPLES 1 TO 7

Resin powders were prepared as described below, respectively, by using Resin Dispersions 1 to 3.

In an round-bottom stainless flask were charged 520 g of the resin dispersion, 4.2 g of a 10 wt. % aqueous solution of poly(aluminum chloride) ("PAC100W", trade name; product of Asada Chemical) and 38 g of 0.02M nitric acid, followed by mixing and dispersing sufficiently by a homogenizer ("Ultra Turrax T50", trade name; product of IKA Works). While stirring in the flask over a heating oil bath, the dispersion was heated to 60° C. After the dispersion was maintained at 60° C. for 30 minutes, 200 g of the resin dispersion was added in portions. The temperature of the heating oil bath was heightened to 90° C., at which the mixture was maintained for a fixed time (spherization time), whereby agglomerated particles were obtained.

After addition of 52 g of 1N sodium hydroxide to the flask, the stainless-made flask was hermetically sealed. While continuing stirring by using a magnetic seal, the mixture was heated to 96° C. The agglomerated particles were fused by maintaining the mixture at that temperature for 7 hours, whereby fused particles were obtained. The average volume particle size ($D_{50}$) of the fused particles was measured using a Coulter counter ("Multisizer II", trade name; product of Nikkaki). These fused particles were washed sufficiently with deionized water (pure water) of pH 6.5. After vacuum lyophilization, the particles were shifted using a 20-μm mesh to yield a resin powder.

The resin powder thus obtained was subjected to the below-described measurements. The average volume particle size ($D_{50}$), average volume particle size distribution GSDv, average number particle size distribution GSDp and a ratio of the particles having a volume particle size of 20 μm or greater were measured using a laser scattering particle size analyzer ("LA-700", product of Horiba, Ltd.), while the shape factor SF1 was measured using a LUZEX image analyzer ("LUZEX III", product of Nireco Corporation).

The surfaceness index was calculated in accordance with the following formula:

(Surfaceness index)=(specific surface area measured)/(specific surface area calculated)

(Specific surface area calculated)=$6\Sigma(n \times R^2)/\{\rho \times \Sigma(n \times R^3)\}$ wherein, n means the number of particles in the channel of a Coulter counter ("TAII", product of Nikkaki), R is the diameter (μm) of the channel of the Coulter counter and ρ is a density of resin particles (g/cm$^3$).

The number-average molecular weight and weight-average molecular weight were each measured using a molecular weight analyzer ("HLC-8120", trade name; product of TOSOH CORP) and the weight-average molecular weight (in terms of polystyrene) was measured with THF as a solvent.

The glass transition temperature was measured using a differential scanning calorimeter ("DSC-50", trade name; product of SHIMADZU CORP.) at a heating rate of 10° C./min.

The compaction ratio was calculated by substituting loosely packed apparent specific gravity X and tightly packed apparent specific gravity Y, as measured by a powder tester (product of Hosokawa Micron), in the following formula:

Compaction ratio=(tightly packed apparent specific gravity Y−loosely packed apparent specific gravity X)/(tightly packed apparent specific gravity Y).

The water content was calculated by accurately weighing (W1) 1 g of a resin powder, drying it at 110° C. for 1 hour in a drier, taking it out from the drier, measuring the drying loss (W2) and substituting (W1) and (W2) in the following formula:

Water content (%)=$(W2/W1) \times 100$.

A volatile content was measured by adding 2 parts by weight of 2-propanol to 1 part by weight of the resin powder, dispersing the mixture for 30 minutes by ultrasonic wave, storing it in a refrigerator (5° C.) for at least one day, conducting solvent extraction, analyzing the supernatant by gas chromatography ("GC-14A", trade name; product of SHIMADZU CORP.) and determining the volatile content in the resin powder.

Analyzing conditions are as follows:
Apparatus: "GC-14A", product of SHIMADZU CORP.
Column: CBP20-M 50-0.25
Detector: FID
Injection amount: 1 to 5 μl
Carrier gas: He (2.5 kg/cm$^2$)
Hydrogen flow rate: 0.6 kg/cm$^2$
Air flow rate: 0.5 kg/cm$^2$
Chart speed: 5 mm/min
Sensitivity: Range 101×Atten 20
Column temperature: 40° C.
Injection Temp: 150° C.

An acid value was measured in accordance with JIS K 0070. Described specifically, a resin powder weighed accurately was charged in a 300 (ml) beaker and 150 (ml) of a 4/1 toluene/ethanol mixture was added to the resin powder to dissolve the latter in the former. Potentiometric titration of the resulting solution was conducted using a 0.1N KOH solution in methanol. This measurement was also conducted for blank. An acid value was determined by the following formula:

$$\text{Acid value (mgKOH/g)} = ((S-B) \times f \times 5.61)/W$$

wherein, W is weight (g) of a resin powder accurately weighed, S is an using amount (ml) of KOH, B is a using amount (ml) of KOH in measurement of blank, and f is the factor of OH.

For judging the amount of impurities in the resin particles, the below-described measurement was conducted. First, 1 g of a resin powder was dissolved in 3 g of acetone. To the resulting solution was added 25 g of deionized water. The precipitate thus formed was filtered off. The solution thus obtained was measured for surface tension and conductivity. The surface tension was measured by a tension meter ("CBVP-Z", trade name; product of Kyowa Kaimen Kagaku), while the conductivity was measured by a conductivity analyzer ("SC400", trade name; product of Yokokawa Electric Corporation).

The measurement results of average volume particle size, average volume particle size distribution GSDv, shape factor SF1, surfaceness index, average number particle size distribution GSDp, a ratio of particles having a volume particle size of 20 μm or greater, number-average molecular weight, weight-average molecular weight, glass transition temperature, compaction ratio, water content, volatile content, acid value, surface tension and conductivity are shown in Table 2.

TABLE 2

|  | Ex. 1 | Ex. 2 | Ex. 3 | Ex. 4 | Ex. 5 | Ex. 6 | Ex. 7 |
|---|---|---|---|---|---|---|---|
| Resin dispersion | 1 | 2 | 3 | 1 | 1 | 1 | 1 |
| Spherizing time | 7 | 7 | 7 | 10 | 7 | 7 | 7 |
| Washing with pure water | done | done | done | done | done | done | done |
| Shifting through 20 μm sieve | done | done | done | done | not done | done | done |
| Vacuum drying time (h) | 8 | 8 | 8 | 8 | 8 | 8 | 4 |
| Average volume particle size (μm) | 6.6 | 6.7 | 6.7 | 6.7 | 6.8 | 6.6 | 6.6 |
| Average volume particle size distribution GSDv | 1.19 | 1.22 | 1.21 | 1.20 | 1.24 | 1.20 | 1.20 |
| Shape factor SF1 | 112 | 112 | 113 | 110 | 113 | 112 | 113 |
| Surfaceness index | 1.35 | 1.54 | 1.48 | 1.34 | 1.45 | 2.08 | 1.35 |
| Average number particle size distribution GSDp | 1.22 | 1.25 | 1.23 | 1.22 | 1.25 | 1.23 | 1.22 |
| Ratio of particles having a volume particle size of 20 μm or greater (%) | 0.04 | 0.06 | 0.05 | 0.04 | 3.8 | 0.04 | 0.04 |
| Number-average molecular weight | $1.1 \times 10^4$ | $2.5 \times 10^3$ | $2.3 \times 10^4$ | $1.1 \times 10^4$ | $1.1 \times 10^4$ | $1.1 \times 10^4$ | $1.1 \times 10^4$ |
| Weight-average molecular weight | $2.5 \times 10^4$ | $3.6 \times 10^3$ | $4.1 \times 10^4$ | $2.5 \times 10^4$ | $2.5 \times 10^4$ | $2.5 \times 10^4$ | $2.5 \times 10^4$ |
| Glass transition temperature (° C.) | 71 | 38 | 59 | 71 | 71 | 71 | 71 |
| Compaction ratio | 0.37 | 0.42 | 0.41 | 0.35 | 0.41 | 0.47 | 0.37 |
| Water content (wt. %) | 0.26 | 0.30 | 0.24 | 0.26 | 0.27 | 0.27 | 3.22 |
| Volatile content (ppm) | 29 | 36 | 32 | 29 | 29 | 52 | 118 |
| Acid value (mg/KOH/g) | 5 | 9 | 22 | 5 | 5 | 5 | 5 |
| Surface tension (mN) | 45 | 42 | 50 | 45 | 45 | 17 | 45 |
| Conductivity (μS) | 52 | 58 | 49 | 52 | 52 | 108 | 53 |
| Polymer | St/Ac | St/Ac | St/Ac | St/Ac | St/Ac | St/Ac | St/Ac |
| Preparation method | EP & A[*1] | EP & A[*1] | EP & A[*1] | EP & A[*1] | EP & A[*1] | EP & A[*1] | EP & A[*1] |
| Smoothness | 4.8 | 4.2 | 4.5 | 4.9 | 4.0 | 4.1 | 3.6 |
| Spreadability | 4.8 | 4.7 | 4.7 | 4.8 | 4.0 | 4.2 | 3.7 |
| Affinity to the skin | 4.9 | 4.7 | 3.6 | 3.2 | 3.9 | 4.4 | 4.6 |
| Odor | 4.1 | 4.0 | 4.1 | 4.1 | 3.9 | 1.8 | 4.1 |

[*1] "EP & A" represents an Emulsion Polymerization and Agglomeration method.

The resin powder thus prepared was applied to the inner arm skin of each of 10 experts constituting a panel and organoleptic tests on smoothness, spreadability, affinity to the skin and odor were conducted. The results are shown in Table 2. In these organoleptic tests, evaluation criteria were set as described below. The numeral indicated in Table 2 is an average value.

Smoothness
  5: Very smooth with excellent dry touch feeling
  4: Very smooth with dry tough feeling
  3: Fair
  2: Poor in smoothness
  1: Not smooth at all Spreadability
  5: Having uniform and good spreadability
  4: Having good spreadability
  3: Fair
  2: Not having good spreadability
  1: Having no spreadability and/or markedly uneven spreadability Affinity to the Skin
Affinity to the skin was evaluated by the following criteria depending on the degree of the dry touch feeling of the skin 30 minutes after application.
  5: Dry touch feeling of the skin remains without deterioration after application
  4: Dry touch feeling of the skin remains though inferior to that upon application
  3: Dry touch feeling of the skin lowers substantially
  2: Dry touch feeling slightly remains on the skin
  1: Dry touch feeling is lost Odor
  5: No odor is detected
  4: A slight but not offensive odor is detected
  3: A slight offensive odor is detected
  2: A little offensive odor is detected
  1: An offensive odor is detected

EXAMPLE 8

After dispersion of 100 parts by weight of a polyester resin made of a bisphenol A propylene oxide adduct, a bisphenol A ethylene oxide adduct and a terephthalic acid derivative and 80 parts by weight of ethyl acetate for 10 minutes, the dispersion was stirred sufficiently (this dispersion was designated as Liquid A). In a ball mill, 60 parts by weight of calcium carbonate was dispersed in 40 parts by water for 10 minutes. In a cooking mixer "MX-915C" (trade name; product of Matsushita Electric Industrial) were charged 7 parts by weight of the resulting calcium carbonate dispersion and 100 parts by weight of a 2% aqueous solution of "Cellogen BS-H" (trade name; product of Daiichi Kogyo Seiyaku) and they were stirred for 5 minutes (the resulting mixture was designated as Liquid B).

Liquids A and B were mixed, each 50 parts by weight, and mixed in a stirrer to obtain a suspension. The solvent was then distilled off under reduced pressure. To the residue was added 10 parts by weight of 6N hydrochloric acid and calcium carbonate was removed. By washing with water, drying and classification, a resin powder having an average particle size of 7.6 μm were obtained.

The measurement results of average volume particle size, average volume particle size distribution GSDv, shape factor SF1, surfaceness index, average number particle size distribution GSDp, a ratio of particles having a volume particle size of 20 μm or greater, number-average molecular weight, weight-average molecular weight, glass transition temperature, compaction ratio, water content, volatile content and acid value are shown in Table 3. Surface tension and conductivity were measured in a similar manner to Examples 1 to 7 except for the use of ethyl acetate as a solvent.

TABLE 3

|  | Ex. 8 | Ex. 9 | Ex. 10 | Comp. Ex. 1 | Comp. Ex. 2 |
| --- | --- | --- | --- | --- | --- |
| Resin dispersion | — | 1 | — | 1 | — |
| Spherizing time | — | 7 | — | 5 | — |
| Washing with pure water | done | done | done | done | — |
| Shifting through 20 μm sieve | done | done | done | done | — |
| Vacuum drying time (h) | 8 | 8 | 8 | 8 | — |
| Average volume particle size (μm) | 6.8 | 6.6 | 6.8 | 6.6 | 7.6 |
| Average volume particle size distribution GSDv | 1.20 | 1.19 | 1.20 | 1.22 | 1.32 |
| Shape factor SF1 | 120 | 112 | 120 | 145 | 146 |
| Surfaceness index | 1.20 | 1.35 | 1.20 | 1.36 | 2.13 |
| Average number particle size distribution GSDp | 1.32 | 1.22 | 1.32 | 1.26 | 1.42 |
| Ratio of particles having a volume particle size of 20 μm or greater (%) | 1.0 | 0.04 | 1.0 | 0.04 | 4.6 |
| Number average molecular weight | $1.1 \times 10^4$ | $1.1 \times 10^4$ | $1.1 \times 10^4$ | $1.1 \times 10^4$ | $4.0 \times 10^3$ |
| Weight average molecular weight | $2.5 \times 10^4$ | $2.5 \times 10^4$ | $2.5 \times 10^4$ | $2.5 \times 10^4$ | $3.0 \times 10^5$ |
| Glass transition temperature (° C.) | 71 | 71 | 71 | 71 | 67 |
| Compaction ratio | 0.45 | 0.37 | 0.45 | 0.62 | 0.63 |
| Water content (wt. %) | 0.25 | 0.26 | 0.25 | 0.29 | 3.19 |
| Volatile content (ppm) | 53 | 29 | 53 | 29 | 25 |
| Acid value (mg/KOH/g) | 21 | 5 | 21 | 5 | 4 |
| Surface tension (mN) | 49 | 45 | 49 | 45 | 60 |
| Conductivity (μS) | 36 | 52 | 36 | 52 | 23 |
| Polymer | PES | St/Ac | PES | St/Ac | PES |
| Preparation method | D & S[2] | EP & A[1] | D & S[2] | EP & A[1] | P[3] |
| Smoothness | 4.3 | 4.8 | 4.5 | 3.3 | 2.6 |
| Spreadability | 4.1 | 4.8 | 4.2 | 3.5 | 2.5 |
| Skin affinity | 4.5 | 4.9 | 4.6 | 3.8 | 3.2 |
| Odor | 2.8 | 4.3 | 4.6 | 4.1 | 4.1 |

[1] "EP & A" represents an Emulsion Polymerization and Agglomeration method.
[2] "D & S" represents a Dissolving and Suspending method.
[3] "P" represents a Pulverization method.

The resin powder thus prepared was subjected to organoleptic tests on smoothness, spreadability, affinity to the skin and odor as in Examples 1 to 7. The results are shown in Table 3.

COMPARATIVE EXAMPLE 1

A resin powder was prepared in a similar manner to Examples 1 to 7 except for decreasing the spherizing time to 5 hours. The resin powder thus obtained was measured for average volume particle size, average volume particle size distribution GSDv, shape factor SF1, surfaceness index, average number particle size distribution GSDp, volume, a ratio of particles having a volume particle size of 20 μm or greater, number-average molecular weight, weight-average molecular weight, glass transition temperature, compaction ratio, water content, volatile content, acid value, surface tension and conductivity. The results are shown in Table 3.

The resin powder thus prepared was subjected to organoleptic tests on smoothness, spreadability, affinity to the skin and odor as in Examples 1 to 7. The results are shown in Table 3.

COMPARATIVE EXAMPLE 2

A polyester polymer (terephthalic acid/bisphenol A propylene oxide adduct/cyclohexanedimethanol) was kneaded in an extruder. The slab thus obtained was rolled and cooled, followed by pulverization by a hammer mill and then a jet mill. The resulting powder was classified by an air classifier and crude and fine powder particles were removed, whereby a resin powder was obtained.

In a similar manner to Examples 1 to 7, the resin powder thus obtained was measured for average volume particle size, average volume particle size distribution GSDv, shape factor SF1, surfaceness index, average number particle size distribution GSDp, a ratio of particles having a volume particle size of 20 μm or greater, number-average molecular weight, weight-average molecular weight, glass transition temperature, compaction ratio, water content, volatile content, acid value, surface tension and conductivity. The results are shown in Table 3.

The resin powder thus prepared was subjected to organoleptic tests on smoothness, spreadability, affinity to the skin and odor as in Examples 1 to 7. The results are shown in Table 3.

EXAMPLES 9 AND 10

In a ball mill, 270 g of each of resin powders obtained in Examples 1 and 8 was mixed with 30 g of mica titanium ("Mearlin MagnaPearl 3000", trade name; product of Engel-Hard Corporation) for 2 hours, whereby resin powders having a surface to which fine particles had been adhered were obtained.

In a similar manner to Examples 1 to 7, the resin powders thus obtained were each measured for average volume particle size, average volume particle size distribution GSDv, shape factor SF1 (prior to adhesion of mica titanium), surfaceness index, average number particle size distribution GSDp, a ratio of particles having a volume particle size of 20 μm or greater, number-average molecular weight, weight-average molecular weight, glass transition temperature, compaction ratio, water content, volatile content, acid value, surface tension and conductivity. The results are shown in Table 3.

The resin powders thus prepared were subjected to organoleptic tests on smoothness, spreadability, affinity to the skin and odor as in Examples 1 to 7. The results are shown in Table 3.

With regard to each of the above-described resin powders, a weak adhesive strength ratio serving as a measure of adhesive strength of the fine particles to the resin particles was calculated as described below. First, in 40 g of pure water was dispersed 2 g of the resin powder composed of fine-particle-adhered resin particles together with a trace amount of a surfactant. Ultrasonic wave was applied to the dispersion at 50 micron ampere by a ultrasonic oscillator inserted in the dispersion. The amount of the metal compound in the supernatant obtained by centrifugation of the resulting dispersion and the amount of the metal compound in the whole fine-particle-adhered resin particles were determined by a fluorescent X-ray analyzer ("SFT-1500", trade name; product of SHIMADZU CORP). A weak adhesive strength ratio was calculated by substituting the above amounts in the following formula: Weak adhesive strength ratio=(amount of metal compound in supernatant separated by ultrasonic wave/amount of metal compound in whole resin particles)×100. As a result, the weak adhesive strength ratio of the resin particles obtained in Example 9 was 65%, while that in Example 10 was 94%.

EXAMPLES 11 TO 15

In each of Examples 11 to 15, talc, mica, titanium oxide, mica titanium, yellow oxide, black oxide, resin particles obtained in Examples 1, 4, 7, 9 and 10, squalane, vaseline, perfume and antiseptic were added in amounts as shown in Table 4, respectively. Components Nos. 1 to 13 in Table 4 were mixed in a Henschel mixer. After addition of a mixture of Components Nos. 14 to 17 (refer to Table 4), they were mixed uniformly, followed by pulverization. The particles thus obtained were formed into a solid powder foundation.

TABLE 4

| No |  | Ex. 11 | Ex. 12 | Ex. 13 | Ex. 14 | Ex. 15 | Comp. Ex. 3 | Comp. Ex. 4 |
|---|---|---|---|---|---|---|---|---|
| 1 | Talc | 14 | 14 | 14 | 14 | 14 | 14 | 14 |
| 2 | Mica | 30 | 30 | 30 | 30 | 30 | 30 | 30 |
| 3 | Titanium oxide | 15 | 15 | 15 | 15 | 15 | 15 | 15 |
| 4 | Mica titanium | 3 | 3 | 3 | — | — | 3 | 3 |
| 5 | Yellow oxide | 1.6 | 1.6 | 1.6 | 1.6 | 1.6 | 1.6 | 1.6 |
| 6 | Black oxide | 0.2 | 0.2 | 0.2 | 0.2 | 0.2 | 0.2 | 0.2 |
| 7 | Ex. 1 | 30 | — | — | — | — | — | — |
| 8 | Ex. 4 | — | 30 | — | — | — | — | — |
| 9 | Ex. 7 | — | — | 30 | — | — | — | — |
| 10 | Ex. 9 | — | — | — | 33 | — | — | — |

TABLE 4-continued

| No | | Ex. 11 | Ex. 12 | Ex. 13 | Ex. 14 | Ex. 15 | Comp. Ex. 3 | Comp. Ex. 4 |
|---|---|---|---|---|---|---|---|---|
| 11 | Ex. 10 | — | — | — | — | 33 | — | — |
| 12 | Comp. Ex. 1 | — | — | — | — | — | 30 | — |
| 13 | Comp. Ex. 2 | — | — | — | — | — | — | 30 |
| 14 | Squalane | 5 | 5 | 5 | 5 | 5 | 5 | 5 |
| 15 | Vaseline | 2.9 | 2.9 | 2.9 | 2.9 | 2.9 | 2.9 | 2.9 |
| 16 | Perfume | 0.1 | 0.1 | 0.1 | 0.1 | 0.1 | 0.1 | 0.1 |
| 17 | Antiseptic | 0.2 | 0.2 | 0.2 | 0.2 | 0.2 | 0.2 | 0.2 |
| | Smoothness | 4.6 | 4.8 | 4.2 | 4.7 | 4.6 | 3.5 | 2.3 |
| | Spreadability | 4.8 | 4.8 | 4.2 | 4.8 | 4.7 | 3.6 | 2.9 |
| | Affinity to the skin | 4.9 | 3.7 | 4.4 | 4.9 | 4.5 | 3.0 | 2.9 |

The solid powder foundations thus obtained were applied to the inner arm skin of 20 female and male experts constituting a panel and their smoothness, spreadability and affinity to the skin was subjected to an organoleptic test. The results are shown in Table 4. The evaluation criteria employed in these tests were similar to those used in Examples 1 to 7.

COMPARATIVE EXAMPLES 3 AND 4

In a similar manner to Examples 11 to 15 except that the resin particles obtained in Comparative Examples 1 and 2 were used instead of the resin particles obtained in Example 1, 4, 7, 9 or 10; and talc, mica, titanium oxide, mica titanium, yellow oxide, black oxide, squalane, vaseline, perfume and antiseptic were added in amounts as shown in Table 4, respectively, solid powder foundations were prepared.

The resulting solid powder foundations were subjected to organoleptic tests for smoothness, spreadability and affinity to the skin as in Examples 11 to 15. Results are shown in Table 4.

It has been understood as the results of Examples 1 to 15 and Comparative Examples 1 to 4 that the resin powders of the invention and solid powder foundations containing them are excellent in spreadability and affinity to the skin; and that spreadability and adhesion upon application can be attained simultaneously. It has also been understood from the results of Examples 9, 10, 14 and 15 that the resin powders composed of fine-particle-adhered resin particles are excellent in spreadability and affinity to the skin, suggesting that the characteristics of the resin particles concerning usability are not lost.

As described above, the resin powder for dermatologic composition according to the invention makes it possible to attain sufficient spreadability and adhesion upon application.

According to the cosmetic composition of the invention, sufficient spreadability and adhesion upon application can be attained, leading to an improvement in usability. In addition, sufficient adhesion makes it possible to prevent makeup from coming off even after application.

According to the skin cleansing composition of the invention, sufficient spreadability and adhesion upon application can be attained, leading to an improvement in usability. In addition, owing to sufficient adhesion, a slight amount of the skin cleansing composition remains on the skin surface even after it is washed away, and as a result, the skin surface has a smooth feeling.

According to the process of the invention for preparing a resin powder for dermatologic composition, a resin powder for dermatologic preparation permitting sufficient spreadability and adhesion can be obtained.

While the invention has been described in detail and with reference to specific examples thereof, it will be apparent to one skilled in the art that various changes and modifications can be made therein without departing from the spirit and scope thereof.

What is claimed is:

1. A cosmetic composition obtained by mixing (a) a resin powder for a dermatologic composition and (b) an additional component selected from the group consisting of squalane, petroleum jelly, liquid paraffin, camellia oil and olive oil, the resin powder comprising resin particles having an average volume particle size of 2 to 20 μm, a shape factor SF1 of 110 to 140 and an average volume particle size distribution GSDv of 1.3 or less,
    wherein a colorant is not present in the resin powder,
    wherein the content of the resin powder is from 0.1 to 60 wt. % of the composition, and
    wherein the additional component is located on an outermost exterior of the resin particles.

2. The cosmetic composition of claim 1, wherein the resin particles further have a surfaceness index of 2.0 or less.

3. The cosmetic composition of claim 1, wherein the resin particles further have an average number particle size distribution GSDp of 1.5 or less.

4. The cosmetic composition of claim 1, wherein a volumetric ratio of the resin particles having a volume particle size of 20 μm or greater is 3% or less.

5. The cosmetic composition of claim 1, wherein a resin constituting the resin particles has a number-average molecular weight of 3,000 to 20,000.

6. The cosmetic composition of claim 1, wherein a resin constituting the resin particles has a weight-average molecular weight of 6,000 to 100,000.

7. The cosmetic composition of claim 1, wherein a resin constituting the resin particles has a glass transition temperature ranging from 40 to 100° C.

8. The cosmetic composition of claim 1, wherein a resin constituting the resin particles has an acid value ranging from 1.0 to 20 mg/KOH/g.

9. The cosmetic composition of claim 1, wherein the resin particles have other fine particles adhered thereto.

10. The cosmetic composition of claim 9, wherein the resin particles and the fine particles are used in combination so as to satisfy the following formula: (volume average particle size of the resin particles)/(volume average particle size of the fine particles)≧2.

11. A skin cleansing composition obtained by mixing (a) a resin powder for a dermatologic composition and (b) an additional component selected from the group consisting of squalane, petroleum jelly, liquid paraffin, camellia oil and olive oil, the resin powder comprising resin particles having an average volume particle size of 2 to 20 μm, a shape factor SF1 of 110 to 140 and an average volume particle size distribution GSDv of 1.3 or less, wherein a colorant is not present in the resin powder, wherein the content of the resin powder is from 0.1 to 60 wt. % of the composition, and wherein the additional component is located on an outermost exterior of the resin particles.

12. The skin cleansing composition of claim 11, wherein the resin particles further have a surfaceness index of 2.0 or less.

13. The skin cleansing composition of claim 11, wherein the resin particles further have an average number particle size distribution GSDp of 1.5 or less.

14. The skin cleansing composition of claim 11, wherein a volumetric ratio of the resin particles having a volume particle size of 20 μm or greater is 3% or less.

15. The skin cleansing composition of claim 11, wherein a resin constituting the resin particles has a number-average molecular weight of 3,000 to 20,000.

16. The skin cleansing composition of claim 11, wherein a resin constituting the resin particles has a weight-average molecular weight of 6,000 to 100,000.

17. The skin cleansing composition of claim 11, wherein a resin constituting the resin particles has a glass transition temperature ranging from 40 to 100° C.

18. The skin cleansing composition of claim 11, wherein the resin particles have other fine particles adhered thereto.

19. The skin cleansing composition of claim 18, wherein the resin particles and the fine particles are used in combination so as to satisfy the following formula: (volume average particle size of the resin particles)/(volume average particle size of the fine particles)≧2.

20. The cosmetic composition of claim 1, wherein the cosmetic composition is obtained by pulverizing a mixture of (a) and (b) after the mixing.

21. The skin cleansing composition of claim 11, wherein the skin cleansing composition is obtained by pulverizing the mixture of (a) and (b).

22. A cosmetic composition obtained by mixing (a) a resin powder for a dermatologic composition and (b) an additional component selected from the group consisting of squalane, petroleum jelly, liquid paraffin, camellia oil and olive oil and subsequently pulverizing the mixture of (a) and (b), the resin powder comprising resin particles having an average volume particle size of 2 to 20 μm, a shape factor SF1 of 110 to 140 and an average volume particle size distribution GSDv of 1.3 or less, wherein a colorant is not present in the resin powder, wherein the content of the resin powder is from 0.1 to 90 wt. % of the composition, and wherein the additional component is located on an outermost exterior of the resin particles.

* * * * *